(12) United States Patent
Suzuki

(10) Patent No.: US 7,938,944 B2
(45) Date of Patent: May 10, 2011

(54) GAS CONCENTRATION MEASUREMENT APPARATUS

(75) Inventor: Yusuke Suzuki, Susono (JP)

(73) Assignee: Toyota Jidosha Kabushiki Kaisha, Toyota (JP)

( * ) Notice: Subject to any disclaimer, the term of this patent is extended or adjusted under 35 U.S.C. 154(b) by 1143 days.

(21) Appl. No.: 10/932,147

(22) Filed: Sep. 2, 2004

(65) Prior Publication Data

US 2005/0061667 A1   Mar. 24, 2005

(30) Foreign Application Priority Data

Sep. 19, 2003   (JP) .................................. 2003-327858

(51) Int. Cl.
*F01N 11/00* (2006.01)
(52) U.S. Cl. ...... 204/426; 204/401; 204/431; 205/784.5
(58) Field of Classification Search .................. 204/401, 204/431, 421, 424–427; 205/784.5; 123/688, 123/690, 693; 702/185, 183
See application file for complete search history.

(56) References Cited

U.S. PATENT DOCUMENTS

| 4,376,026 | A | * | 3/1983 | Hoffman et al. ............... 204/407 |
| 4,724,814 | A | * | 2/1988 | Mieno et al. .................. 123/688 |
| 5,928,494 | A | * | 7/1999 | Kato et al. ..................... 205/781 |
| 6,551,499 | B1 | * | 4/2003 | Springhorn et al. ........ 205/784.5 |
| 2003/0121310 | A1 | * | 7/2003 | Tomura et al. ................ 73/31.05 |
| 2004/0047396 | A1 | * | 3/2004 | Nomura et al. .................. 374/141 |
| 2004/0089545 | A1 | * | 5/2004 | Kawase et al. ................. 204/425 |

FOREIGN PATENT DOCUMENTS

| DE | 37 10 154 A1 | 10/1987 |
| EP | 0 892 265 A1 | 1/1999 |
| JP | B2 7-69288 | 7/1995 |
| JP | B2 2505152 | 4/1996 |
| JP | A 2000-193635 | 7/2000 |
| JP | A 2000-214130 | 8/2000 |
| JP | A 2003-232771 | 8/2003 |

* cited by examiner

*Primary Examiner* — Ula C Ruddock
*Assistant Examiner* — J. Christopher Ball
(74) *Attorney, Agent, or Firm* — Oliff & Berridge, PLC

(57) ABSTRACT

A first cell having an electrolyte and a pair of electrodes on the surface of the electrolyte with one of the electrodes facing a gas chamber causes, upon receipt of an applied voltage, a current to flow in accordance with the amount of oxygen discharge while discharging oxygen from the chamber. An open-circuit-induced fault is detected in accordance with a current flow change that is caused by the first cell when the voltage applied to the first cell reverts to a reference level after a temporary deviation from the reference level. A second cell generates a signal in accordance with the oxygen concentration in the measurement target gas chamber. An open-circuit-induced fault is detected in accordance with a signal change that is generated from the second cell when the voltage applied to the first cell reverts to a reference level after a temporary deviation from the reference level.

10 Claims, 4 Drawing Sheets

Normal

Current according to air-fuel ratio

Open circuit formed

0

Normal

Current according to Nox concentration

Open circuit formed

0

GAS CONCENTRATION MEASUREMENT APPARATUS

BACKGROUND OF THE INVENTION

1. Field of the Invention

The present invention relates to a gas concentration measurement apparatus, and more particularly to a fault detection technology for detecting a fault in a gas concentration apparatus.

2. Background Art

A conventional NOx concentration sensor for detecting the NOx concentration in an exhaust gas is disclosed, for instance, by Japanese Patent Laid-open No. 2000-214130 (hereinafter referred to as "Patent Document 1"). In this NOx concentration sensor, a pump cell is positioned upstream of a measurement target gas chamber while a sensor cell is positioned downstream of the measurement target gas chamber. The pump cell and sensor cell both comprise a solid electrolyte and a pair of electrodes that are mounted on the surface of the solid electrolyte. When a predetermined voltage is applied between the electrodes, the pump cell discharges (pumps) oxygen out of the measurement target gas chamber and causes a current to flow in accordance with the amount of the discharged oxygen. The sensor cell, on the other hand, resolves NOx, which exists in the measurement target gas chamber, into nitrogen and oxygen. When a predetermined voltage is applied between the electrodes, the sensor cell discharges the oxygen from the measurement target gas chamber and causes a current to flow in accordance with the amount of the discharged oxygen.

First of all, the pump cell of the above NOx concentration sensor removes remaining oxygen from an exhaust gas that enters the measurement target gas chamber. When the exhaust gas reaches the sensor cell after oxygen removal, NOx in the exhaust gas is resolved into nitrogen and oxygen. The sensor cell then generates a current in accordance with the resulting amount of oxygen, that is, the amount of NOx in the exhaust gas. Therefore, the above NOx concentration sensor can measure the NOx concentration in the exhaust gas in accordance with the value of a current flow in the sensor cell.

At present, the NOx concentration sensor is regarded as an important sensor for controlling an internal combustion engine in accordance with the information detected by the sensor and guaranteeing the emission from an internal combustion engine. It is therefore necessary that the NOx concentration sensor properly function at all times. It is demanded that any fault existing in the NOx concentration sensor be accurately detected. Particularly, an open circuit is a fundamental fault and should be detected early.

As a fault detection method for the pump cell of the NOx concentration sensor, the current flowing when the air-fuel ratio indicates a known predefined operating state (in which an output is always generated when no abnormality exists) may be measured and compared against a judgment value. However, it is difficult to determine during a vehicle run whether the above predefined operating state prevails. Even if such determination is accomplished, no fault detection can be achieved until the predefined operating state arises.

If the output current continues to be zero, a common sensor fault detection method may be used to conclude that there is an open circuit in the sensor. In the NOx concentration sensor, however, the output currents of both the pump cell and sensor cell may be zero from the viewpoint of control. If, for instance, the air-fuel ratio is stoichiometric, the pump cell's output current (pump cell current) is zero. Even when there is an open circuit, the apparent output current does not continue to be zero due, for instance, to surrounding noise. Particularly, the output current of the sensor cell (sensor cell current) is as small as several hundred nA even when the sensor cell is properly functioning. It is therefore difficult to detect an open circuit by determining whether the output current remains zero.

A fault detection method for use with sensors other than the NOx concentration sensor may be applied to the NOx concentration sensor. For an $O_2$ sensor, a fault detection method disclosed, for instance, by Japanese Patent Publication No. Hei 7-69288 (hereinafter referred to as "Patent Document 2") is known. For an air-fuel ratio sensor, a fault detection method disclosed, for instance, by Japanese Patent No. 2505152 (hereinafter referred to as "Patent Document 3") is known. The fault detection method disclosed by Patent Document 2 raises a voltage present at one end of the sensor to check for a resulting change in the DC current for open-circuit detection purposes. The fault detection method disclosed by Patent Document 3 operates an air pump to supply atmospheric air to the inside of a sensor housing while the exhaust gas air-fuel ratio is in a steady state, thereby forcibly changing the pump cell current. The actual pump cell current detected at the time of atmospheric air supply is used to determine whether the pump cell is faulty. Further, the detected output voltage change in a sensing cell is used to determine whether the sensing cell is faulty.

However, the fault detection method disclosed by Patent Document 2 cannot readily be applied to an NOx concentration sensor such as a pump-cell-based sensor. For the voltage-current characteristic exhibited by the pump cell, there is a limiting current region in which the current is substantially constant relative to the voltage, and the voltage applied to the pump cell is controlled so that the pump cell current is within the limiting current region. Therefore, even if the voltage at one end is raised as is the case with a method disclosed by Patent Document 2, the pump cell current remains virtually unchanged. If, on the contrary, the pump cell current increases in accordance with the voltage, the pump cell current exceeds the limiting current. In such an instance, oxygen molecules may be pumped out of a solid electrolyte to incur blackening of the solid electrolyte, thereby causing the pump cell to deteriorate.

The method disclosed by Patent Document 3 is applied to an air-fuel ratio sensor that uses a pump cell as is the case with the NOx concentration sensor. However, the method disclosed by Patent Document 3 has a disadvantage, which will now be described. To detect a fault, the method disclosed by Patent Document 3 supplies atmospheric air from the outside to forcibly vary the pump cell current (limiting current) and checks whether the output value of the pump is within a predetermined range. For fault detection purposes, it is therefore necessary that the air-fuel ratio be in a steady state. It means that the opportunity for fault detection is limited. The air-fuel ratio may continue to be unstable for an extended period of time depending on the operating status of an internal combustion engine. It is therefore preferred that sensor fault detection be achievable without regard to the air-fuel ratio. Further, the method disclosed by Patent Document 3 cannot restore the normal control state until atmospheric air leaves the sensor housing after fault detection, causing the internal air-fuel ratio to revert to the original value. The information detected by the NOx concentration sensor and air-fuel ratio sensor is important for internal combustion engine control. Therefore, the period during which the sensor's gas concentration measurement function is rendered inoperative subsequently to fault detection should be minimized.

SUMMARY OF THE INVENTION

The present invention has been made to solve the above problems and provide a gas concentration measurement apparatus that is capable of accurately detecting an open-circuit-induced fault without regard to the air-fuel ratio and resuming a normal gas concentration measurement operation within a short period of time after fault detection.

In accordance with a first aspect of the present invention, the gas concentration measurement apparatus comprises a cell. The cell comprises a solid electrolyte and a pair of electrodes on the surface of the solid electrolyte with one of the electrodes facing a measurement target gas chamber and causes, upon receipt of an applied voltage, a current to flow in accordance with the amount of oxygen discharge while discharging oxygen from the measurement target gas chamber. The gas concentration measurement apparatus further comprises a power supply for applying a voltage to the cell; voltage variation means for varying the voltage to be applied to the cell; current measurement means for measuring the current caused by the cell; and fault detection means for detecting a fault in the cell in accordance with a change in the current caused by the cell when the voltage applied to the cell reverts to a reference level after a temporary deviation from the reference level.

In accordance with a second aspect of the present invention, the gas concentration measurement apparatus comprises a first cell and a second cell. The first cell comprises a solid electrolyte and a pair of electrodes on the surface of the solid electrolyte with one of the electrodes facing a measurement target gas chamber and causes, upon receipt of an applied voltage, a current to flow in accordance with the amount of oxygen discharge while discharging oxygen from the measurement target gas chamber. The second cell generates a signal in accordance with the oxygen concentration in the measurement target gas chamber. The gas concentration measurement apparatus further comprises a power supply for applying a voltage to the first cell; voltage variation means for varying the voltage to be applied to the first cell; second cell output signal measurement means for measuring a signal that is generated from the second cell; and second cell fault detection means for detecting a fault in the second cell in accordance with a change in the signal generated from the second cell when the voltage applied to the first cell reverts to a reference level after a temporary deviation from the reference level.

DESCRIPTION OF THE PREFERRED EMBODIMENT

An embodiment of the present invention will now be described with reference to the accompanying drawings.

Figure 1:
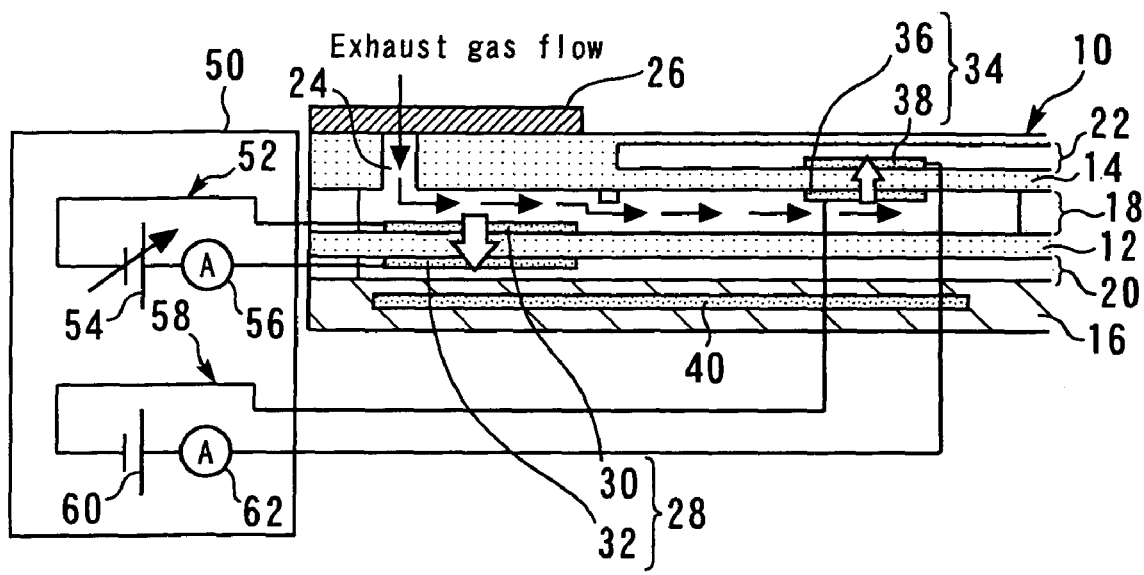
FIG. 1 illustrates the configuration of one embodiment of a gas concentration measurement apparatus according to the present invention.

FIG. 1 illustrates the configuration of one embodiment of a gas concentration measurement apparatus according to the present invention. The gas concentration measurement apparatus 10 shown in FIG. 1 is positioned in an exhaust path of an internal combustion engine to measure the NOx concentration in an exhaust gas that is discharged from the internal combustion engine. The gas concentration measurement apparatus 10 includes zirconia layers 12, 14, which are solid electrolytes, and an insulation layer 16. A measurement target gas chamber 18 is provided between the two zirconia layers 12, 14. Atmospheric air chambers 20, 22 are formed next to the zirconia layers 12, 14. These atmospheric air chambers 20, 22 are isolated from the measurement target gas chamber 18 by the zirconia layers 12, 14.

The gas concentration measurement apparatus 10 is provided with a diffusion hole 24 that leads to the measurement target gas chamber 18. The diffusion hole 24 is path for introducing the gas to be processed, that is, the exhaust gas. The diffusion hole 24 communicates with the internal combustion engine's exhaust path via a diffusion resistance layer 26. The diffusion resistance layer 26 is a porous material for governing the speed of exhaust gas diffusion within the exhaust path. When the configuration described above is employed, the exhaust gas in the exhaust path diffuses within the measurement target gas chamber 18 at a speed that is governed by the diffusion hole 24 and diffusion resistance layer 26.

The exhaust gas introduced from the diffusion hole 24 flows along a predetermined route and into the measurement target gas chamber 18. This route is provided with a pump cell 28 as the first cell. The pump cell 28 comprises a zirconia layer 12, a pump electrode 30, and an atmospheric air electrode 32. The pump electrode 30 and atmospheric air electrode 32 are positioned on both sides of the zirconia layer 12. The pump electrode 30 is made of a Pt—Au alloy and exposed to the measurement target gas chamber 18. The atmospheric air electrode 32 is made of Pt and exposed to an atmospheric air chamber 20.

A sensor cell 34 is positioned downstream of the pump cell 28 as the second cell. The sensor cell 34 comprises a zirconia layer 14, a sensor electrode 36, and an atmospheric air electrode 38. The sensor electrode 36 and atmospheric air electrode 38 are positioned on both sides of the zirconia layer 14. The sensor electrode 36 is made of a Pt—Rh alloy and exposed to the measurement target gas chamber 18. The atmospheric air electrode 38 is made of Pt and exposed to an atmospheric air chamber 22.

When the pump electrode 30 of the pump cell 28 reaches a specified activity temperature, the pump cell 28 ionizes oxygen in the exhaust gas and resolves $NO_2$ in the exhaust gas to obtain NO. When the sensor electrode 36 of the sensor cell 34 reaches a specified activity temperature, the sensor cell 34 resolves NO in the exhaust gas into nitrogen and oxygen ions. The gas concentration measurement apparatus 10 has a heater 40 inside the insulation layer 16 to heat the electrodes to their activity temperatures.

The gas concentration apparatus 10 according to the present embodiment includes an ECU (Electronic Control Unit) 50. The ECU 50 has a drive circuit 52 for the pump cell

28. The drive circuit 52 includes a variable power supply 54 and an ammeter (first cell current measurement means) 56. The variable power supply 54 applies a voltage, which is directed from the atmospheric air electrode 32 to pump electrode 30, between the pump electrode 30 and atmospheric air electrode 32. The ammeter 56 measures the current flow between the pump electrode 30 and atmospheric air electrode 32.

The ECU 50 has a drive circuit 58 for the sensor cell 34. This drive circuit 58 includes a power supply 60 and an ammeter (second cell output signal measurement means) 62. The power supply 60 applies a voltage, which is directed from the atmospheric air electrode 38 to the sensor electrode 36, between the sensor electrode 36 and atmospheric air electrode 38. The ammeter 62 detects a current flow between the sensor electrode 36 and atmospheric air electrode 38.

The ECU 50 according to the present embodiment has two control modes: gas concentration measurement mode and open-circuit detection mode. The gas concentration measurement mode is a control mode for measuring the NOx concentration in the exhaust gas, which is a primary function of the gas concentration measurement apparatus 10. This mode is regarded as a basic control mode. On the other hand, the open-circuit detection mode is a control mode for detecting an open-circuit-induced fault in the gas concentration measurement apparatus 10. This mode is periodically activated at predetermined intervals.

Figure 2:
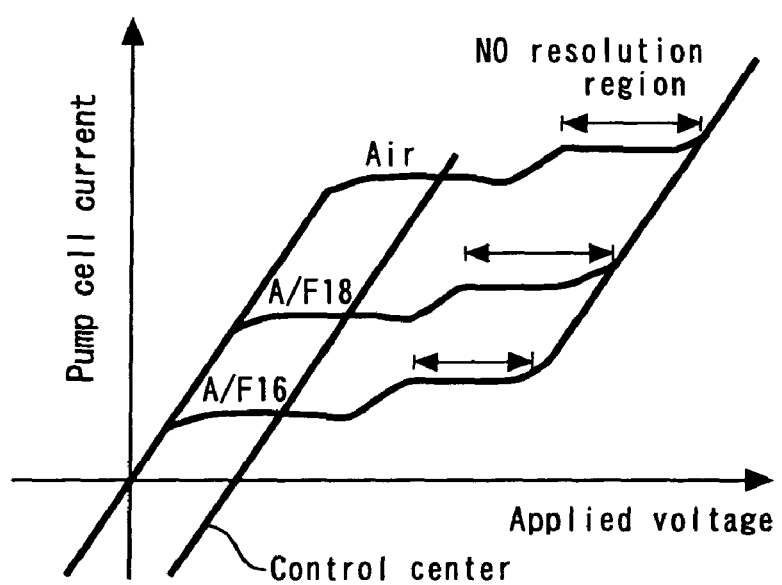
FIG. 2 illustrates the voltage-current characteristic of a pump cell included in the apparatus of FIG. 1.

The control exercised in the gas concentration measurement mode will now be described with reference to FIG. 2. FIG. 2 is a graph that uses the exhaust gas air-fuel ratio as a parameter and illustrates the relationship between the voltage applied between the atmospheric air electrode 32 and pump electrode 30 of the pump cell 28 and the current flow in the pump cell 28 (hereinafter referred to as the "pump cell current"). In FIG. 2, the curves designated "A/F16" and "A/F18" represent the voltage-current characteristics of an exhaust air-fuel ratio of 16 and an exhaust air-fuel ratio of 18, respectively. The curve designated "Air" represents the voltage-current characteristic that prevails when the gas to be measured is pure air.

When heated to the activity temperature described earlier, the pump electrode 30 resolves $NO_2$ in the measurement target gas chamber 18 into NO and oxygen. In a state prevailing when the activity temperature is reached by the pump electrode 30, therefore, the oxygen originally contained in the exhaust gas and the oxygen generated when $NO_2$ is resolved both exist around the pump electrode 30. When a voltage is applied by the variable power supply 54, the pump cell 28 pumps the oxygen within the measurement target gas chamber 18 to discharge it into atmospheric air chamber 20. In this instance, a current flows in the pump cell 28 in accordance with the amount of discharged oxygen.

All the curves in FIG. 2 indicate that the pump cell current has a convergence value with respect to an increase in the applied voltage. This convergence value corresponds to a current value that prevails when the entire oxygen in the exhaust gas is ionized and discharged. To let the pump cell 28 efficiently remove the oxygen from the exhaust gas, therefore, it is necessary to apply an appropriate voltage to the atmospheric air electrode 32 in accordance with the exhaust gas air-fuel ratio so that the pump cell current reaches the convergence value. The convergence value for the pump cell current is hereinafter referred to as the limiting current.

The NO resolution region shown in FIG. 2 represents a region in which NO as well as the $NO_2$ contained in the exhaust gas are resolved into nitrogen and oxygen. To let the sensor cell 34 cause a current flow according to the NOx concentration, it is necessary that the pump cell 28 resolve $NO_2$ only and allow NO to reach the sensor cell 34 as it is. Therefore, the voltage applied to the atmospheric air electrode 32 of the pump cell 28 must be lower than for the NO resolution region.

In order to enable accurate measurement of the NOx concentration, in the gas concentration measurement mode, the ECU 50 controls the voltage applied to the atmospheric air electrode 32 in such a manner as to satisfy the above-mentioned requirements. For example, two application voltage control methods may be used in the gas concentration measurement mode. One method determines an application voltage that satisfies the above requirements at all air-fuel ratios and constantly uses the determined application voltage as the application voltage for the gas concentration measurement mode. The other method determines a set of application voltages for all air-fuel ratios satisfying the above requirements as indicated by the control center in FIG. 2 and controls the application voltage in accordance with the air-fuel ratio and in compliance with the control center straight line. Since a pump cell current according to the oxygen concentration in the measurement target gas chamber 18 flows in the pump cell 28, the air-fuel ratio can be detected in accordance with the pump cell current.

Figure 3A:
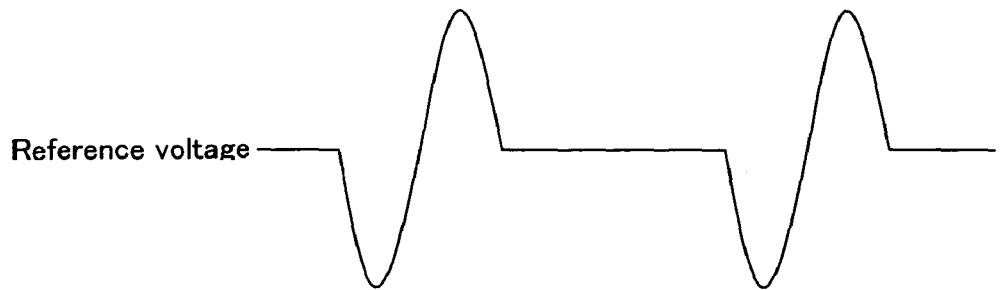
FIGS. 3A and 3B illustrate examples of a waveform of a voltage to be applied to the pump cell in an open-circuit detection mode.

The open-circuit detection mode, which is peculiar to the present embodiment of the gas concentration measurement apparatus 10, will now be described with reference to FIGS. 3A through 7. FIG. 3A illustrates the application characteristic of a voltage that is applied from the variable power supply 54 to the atmospheric air electrode 32 of the pump cell 28 in the open-circuit detection mode. As shown in FIG. 3A, the voltage to be applied to the atmospheric air electrode 32 is swept vertically at a specified amplitude around a reference voltage in the open-circuit detection mode. It is accomplished by superposing an AC component, which periodically changes at a specified amplitude, over the reference voltage. The reference voltage represents an application voltage setting that is selected for the above-mentioned gas concentration measurement mode.

Figure 4:
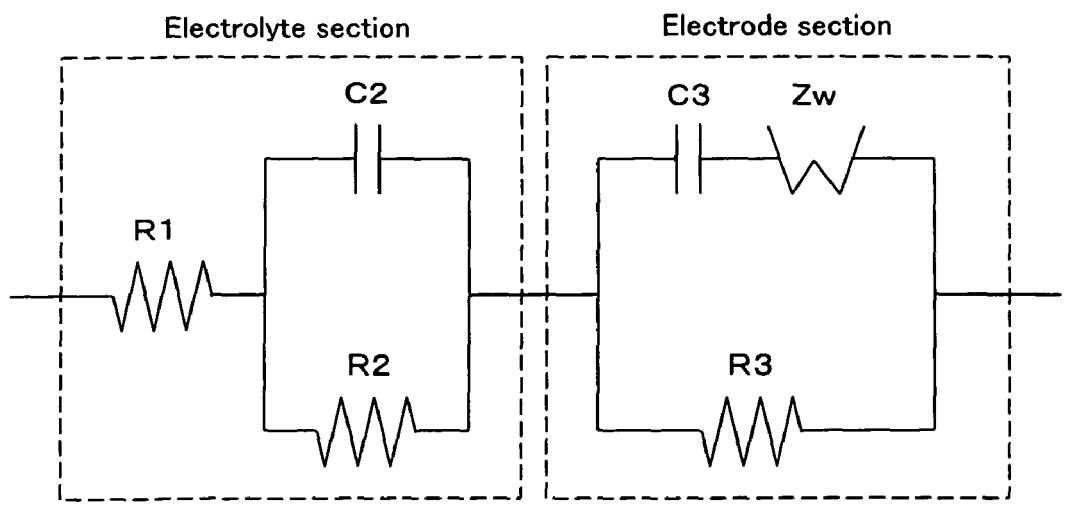
FIG. 4 illustrates an equivalent circuit of the pump cell.

The reason for varying the application voltage in an alternating current manner as indicated in FIG. 3A can be explained with reference to FIG. 4. FIG. 4 illustrates an equivalent circuit of the pump cell 28 or sensor cell 34. It is assumed herein that the figure shows an equivalent circuit of the pump cell 28. As shown in FIG. 4, the pump cell 28 can be indicated as a circuit that is formed by connecting its electrolyte section (zirconia layer 12) in series with an electrode section (pump electrode 30 and atmospheric air electrode 32). The electrolyte section can be indicated as a circuit in which element R1 is connected in series with a parallel circuit of elements C2 and R2. Element R1 is a resistance component of solid electrolyte grains (bulk). Element R2 is a resistance component of a grain boundary of the solid electrolyte. Element C2 is a capacitance component of a grain boundary. The electrode section can be indicated as a circuit in which element R3 is connected in parallel with a series circuit of elements C3 and Zw. Element R3 is a resistance component of an electrode interface. Element C3 is a capacitance component of the electrode interface. Element Zw is an impedance component that is generated due to periodic interface concentration changes, which are caused when polarization occurs upon AC component application.

In the above-mentioned gas concentration measurement mode, a constant DC voltage according to the air-fuel ratio is applied to the circuit. In this instance, the constant voltage is also applied to elements C2 and C3, which are capacitance components. Therefore, no current flows to elements C2 and C3. The current flows to the element R2 side of the parallel circuit of the electrolyte section. In the electrode section, the current flows to the element R3 side. As a result, when the whole circuit is viewed, it is found that a steady-state current flows to elements R1, R2, and R3. This current corresponds to the above-mentioned limiting current according to the air-fuel ratio.

According to the equivalent circuit shown in FIG. 4, it is conceivable that the magnitude of the current varies with the magnitude of the applied voltage even when a DC voltage is applied as is the case with the gas concentration measurement mode. However, the application voltage setting range is limited, as described earlier, so that the pump cell current can converge to a limiting current depending on the exhaust gas air-fuel ratio and the voltage does not reach the NO resolution region. Therefore, the pump cell current cannot be significantly varied from the limiting current simply by raising or lowering the DC voltage.

If an AC component is added to the application voltage as indicated in FIG. 3A, the voltage applied across elements C2 and C3 varies in an alternating current manner. Therefore, a current flows to elements C2 and C3 in accordance with the changes in the application voltage. As a result, the current flow in the whole circuit greatly varies with the changes in the current flow in elements C2 and C3. In contrast to cases where the DC voltage is merely raised or lowered, the current can be greatly varied by small changes in the application voltage. The resulting current variation range (amplitude) increases with an increase in the frequency of the AC component of the application voltage.

Figure 5A:
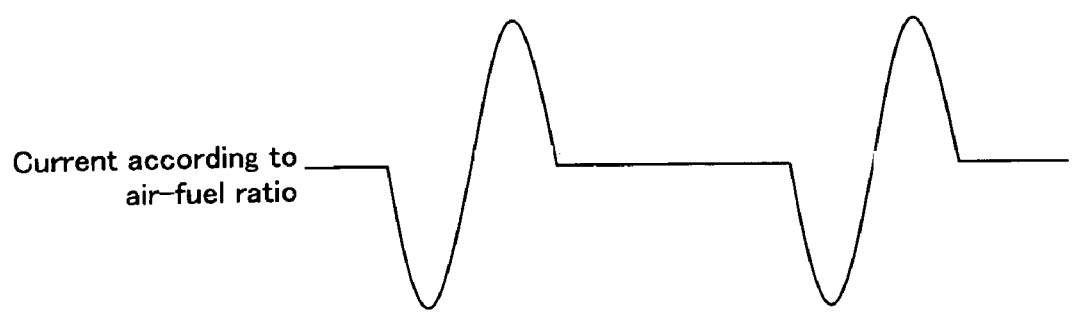
FIGS. 5A and 5B illustrate pump cell current changes when the application voltage varies as shown in FIG. 3A.
Figure 5B:

FIGS. 5A and 5B show pump cell current changes that are measured by the ammeter 56. If the application voltage varies as shown in FIG. 3A while the pump cell 28 functions normally with no open circuit formed, the pump cell current varies vertically in an alternating current manner around the limiting current according to the prevalent air-fuel ratio and exhibits the same waveform as the application voltage as indicated in FIG. 5A. If the air-fuel ratio is stoichiometric, the pump cell current varies vertically around the zero output point.

If there is an open circuit somewhere in the pump cell 28, no current flows to the pump cell 28. Consequently, the waveform of the pump cell current measured by the ammeter 56 remains at the zero output level as indicated in FIG. 5B without regard to the changes in the application voltage. The magnitude of the current depends on the air-fuel ratio. However, the current may change without regard to the air-fuel ratio. Changes in the current are determined depending on whether there is an open circuit in the pump cell 28. Therefore, an open-circuit-induced fault in the pump cell 28 can be accurately detected by determining whether the pump cell current changes when the application voltage is varied as indicated in FIG. 3A.

In the open-circuit detection mode, the sensor cell 34 is checked for a fault that results from an open circuit. The sensor cell 34 not only resolves the NO in the exhaust gas into nitrogen and oxygen, but also ionizes the oxygen in the exhaust gas. Therefore, the sensor cell current varies not only with the NOx concentration in the measurement target gas chamber 18 but also with the oxygen concentration. When the application voltage varies in an alternating current manner as described earlier, the pump cell current also varies in an alternating current manner as far as the pump cell 28 is normal. In such an instance, the number of oxygen ions pumped out of the measurement target gas chamber 18 by the pump cell 28 also varies with the changes in the pump cell current. In other words, when the application voltage increases, causing an increase in the pump cell current, an increased number of oxygen ions are pumped. When the application voltage decreases, causing a decrease in the pump cell current, a decreased number of oxygen ions are pumped. Therefore, the oxygen concentration in the measurement target gas chamber 18 changes to a waveform that is an inverse of the waveform of the application voltage. The limiting current represents a current value that prevails when the oxygen existing in the measurement target gas chamber 18 is ionized almost entirely and pumped. Thus, the oxygen concentration in the measurement target gas chamber 18 is theoretically zero. Therefore, when the pump cell current becomes larger than the limiting current, the oxygen concentration in the measurement target gas chamber 18 is a minus value. In such an instance, however, water molecules contained in the exhaust gas instead of oxygen are resolved into oxygen ions and hydrogen ions. The resulting oxygen ions are then pumped by the pump cell 28.

Figure 6A:
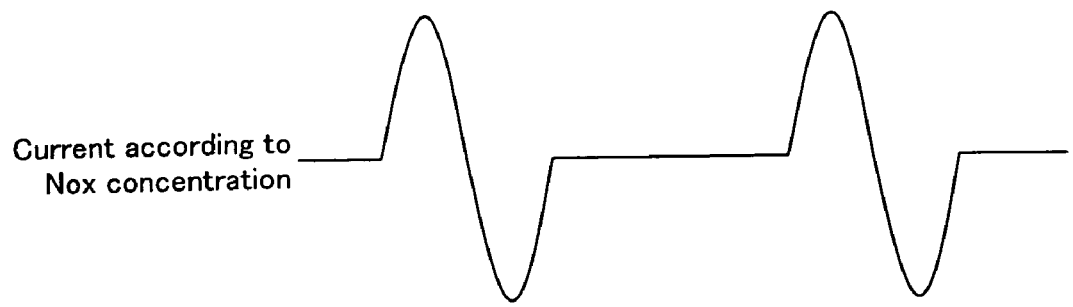
FIGS. 6A and 6B illustrate sensor cell current changes when the application voltage varies as shown in FIG. 3A.
Figure 6B:
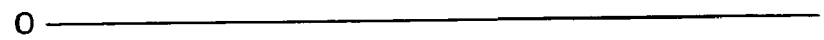

FIGS. 6A and 6B show sensor cell current changes that are measured by the ammeter 62. As described earlier, the sensor cell current also varies with the oxygen concentration in the measurement target gas chamber 18. Therefore, while the sensor cell 34 functions normally with no-open circuit formed, the sensor cell current normally corresponds to the NOx concentration value. However, when the application voltage is changed as indicated in FIG. 3A, the sensor cell current changes to a waveform that is an inverse of the waveform of the application voltage as indicated in FIG. 6A. When the pump cell current increases above the limiting current, the water molecules resolve so that the hydrogen ion concentration in the measurement target gas chamber 18 increases. If hydrogen ions exist near the sensor electrode 36, an electromotive force, which is oriented in a direction opposite to that of the power supply 60, is generated in the sensor cell 34 so that a sensor cell current flows in a minus direction. Oxygen ions are then pumped from the atmospheric air electrode 38 to the sensor electrode 36. The magnitude of the sensor current oriented in the minus direction increases in accordance with the hydrogen ion concentration. The hydrogen ion concentration increases in accordance with the application voltage. As a result, the waveform shown in FIG. 6A is obtained.

If there is an open circuit somewhere in the sensor cell 34, no current flows to the sensor cell 34. Consequently, the waveform of the sensor cell current measured by the ammeter 62 remains at the zero output level as indicated in FIG. 6B without regard to the changes in the oxygen concentration (or hydrogen ion concentration) in the measurement target gas chamber 18. Therefore, an open-circuit-induced fault in the sensor cell 34 can be accurately detected by determining whether the sensor cell current changes when the application voltage is varied as indicated in FIG. 3A.

Figure 3B:

A fault in the pump cell 28 or sensor cell 34 can be detected by checking whether the current varies when the application voltage is varied. Therefore, the purpose is attained simply by varying the application voltage in a single direction as indicated in FIG. 3B instead of varying the application voltage in both the upward and downward directions as indicated in FIG. 3A. In other words, the application voltage according to the present invention need not always be varied in an alternating current manner or in such a manner as to draw a sine wave. The purpose is achieved by restoring the application voltage to a reference level after a temporary deviation from the reference level. However, when the application voltage is varied in a single direction as indicated in FIG. 3B, a considerable time lag occurs between the instant at which the application voltage reverts to the reference level and the instant at which the oxygen concentration in the measurement target gas chamber 18 reverts to the previous oxygen concentration level. However, when the application voltage is varied in one direction and then varied in a reverse direction as indicated in FIG. 3A, the oxygen concentration is forcibly varied in the reverse direction to promptly recover the previous concentration level. As a result, it is possible to promptly revert to normal control in the gas concentration measurement mode.

Figure 7:
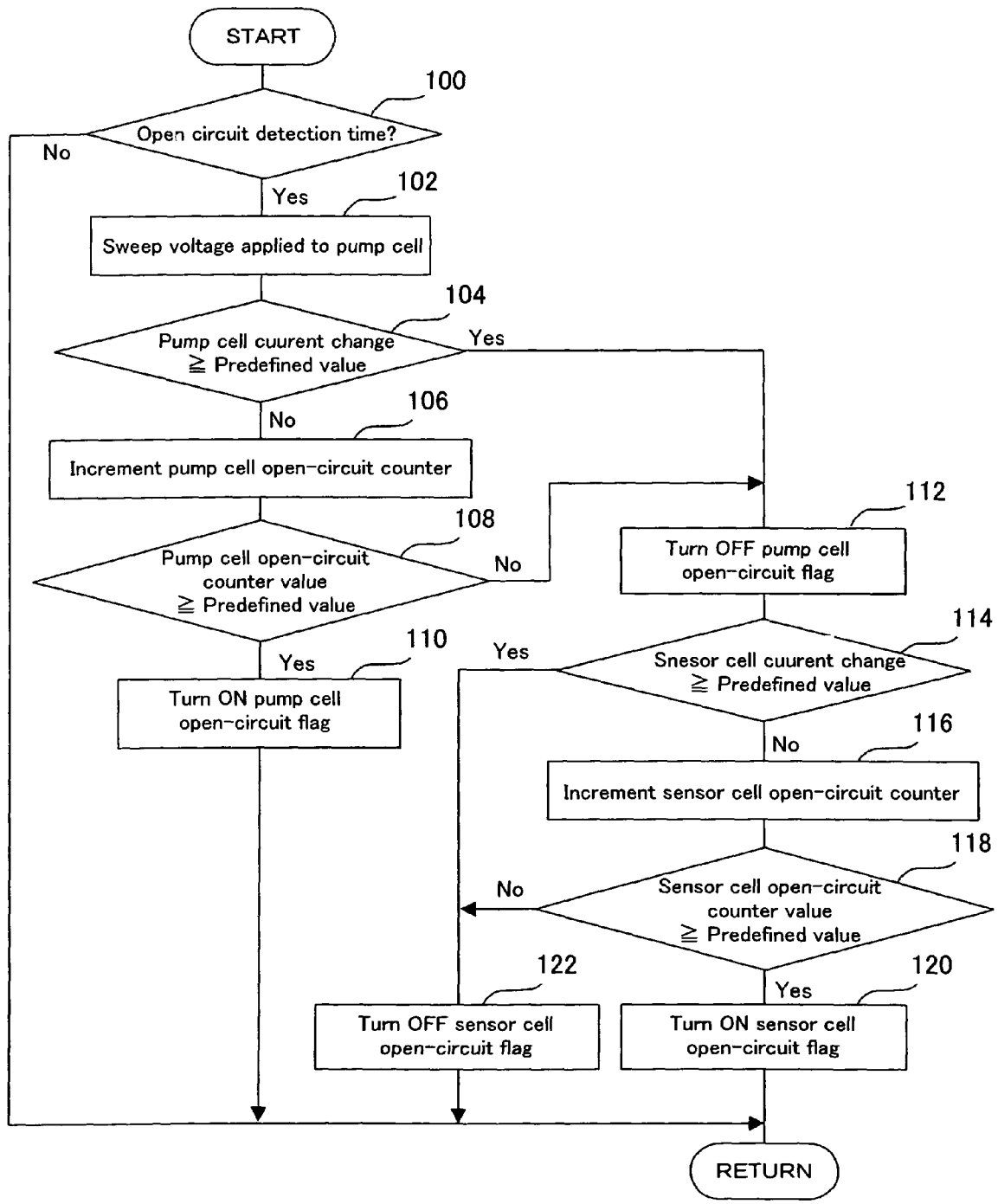
FIG. 7 illustrates a flowchart for an open-circuit detection routine to be performed in embodiments.

The control process in the open-circuit detection mode, which has been described above, is exercised in the ECU 50 by performing a routine indicated in a flowchart shown in FIG. 7. In the routine shown in FIG. 7, step 100 is first performed to check whether the time for open-circuit detection has come. While the open-circuit detection mode is activated, the NOx concentration measurement function, which is a primary function of the gas concentration measurement apparatus 10, cannot be exercised. Therefore, the open-circuit detection mode is not frequently activated but activated periodically at appropriate time intervals. The ECU 50 measures, for instance, the operating time since the last activation of the open-circuit detection mode. When a predetermined period of time elapses, the ECU 50 concludes that the time for open-circuit detection has come.

When the time for open-circuit detection has come, the variable power supply 54 sweeps the voltage applied to the pump cell 28 as indicated in FIG. 3A or 3B (step 102). In this instance, the ammeter 56 measures the changes in the pump cell current. Step 104 is then performed to check whether the amount of a change in the pump cell current at a predetermined sampling time is equal to or greater than a predefined value. An open-circuit is detected by determining the magnitude of a change in the pump cell current and not by checking whether there is a change in the pump cell current. Open-circuit detection is achieved in such a manner for the purpose of preventing noise-induced current changes from being erroneously interpreted as current changes caused by application voltage changes. It is assumed that the amount of a change at a predetermined sampling time is compared against a predefined value. Alternatively, however, as the magnitude of the change in the pump cell current, the maximum change amount of the pump cell current or the difference between the maximum and minimum change amounts may be compared against a predefined value.

The greater the predefined value used in step 104, the higher the degree to which the influence of noise can be suppressed. If a small current change is caused by a change in the application voltage, an erroneous judgment might be formed to conclude that an open circuit is encountered. Therefore, if it is found in step 104 that the amount of a pump cell current change is smaller than predefined, it is not immediately concluded that there is an open circuit in the pump cell 28, but proceeds to perform steps 106 and 108. More specifically, step 106 is performed to increment a pump cell open-circuit counter, which indicates the number of times query step 104 has been satisfied, and then step 108 is performed to check whether the pump cell open-circuit counter has reached a predefined value. When the predefined value is reached by the pump cell open-circuit counter, step 110 is performed to turn ON a pump cell open-circuit flag. It is then judged that there is an open circuit in the pump cell 28. This judgment result appears, for instance, on a display device that is disposed in a vehicle interior.

If it is found in step 104 that the amount of a pump cell current change is not smaller than predefined, or if it is found in step 108 that the pump cell open-circuit counter value is smaller than predefined, it is concluded that the pump cell 28 is functioning normally. In such an instance, the pump cell open-circuit flag turns OFF in step 112. Then, processing steps 114 and beyond are performed to judge whether there is an open circuit in the sensor cell 34. More specifically, step 114 is performed to judge whether the amount of a sensor cell current change at a predetermined sampling time is equal to or greater than a predefined value. The sensor cell current is measured by the ammeter 62 when the voltage applied to the pump cell 28 is swept in step 102. A judgment is formulated in accordance with the magnitude of a sensor cell current change for the purpose of preventing noise-induced current changes from being erroneously interpreted as current changes caused by application voltage changes. It is assumed that the amount of a change at a predetermined sampling time is compared against a predefined value. Alternatively, however, as the magnitude of the change in the sensor cell current, the maximum change amount of the sensor cell current or the difference between the maximum and minimum change amounts may be compared against a predefined value.

If it is found in step 114 that the amount of a sensor cell current change is smaller than the predefined value, it is not immediately concluded that there is an open circuit in the sensor cell 34. However, step 116 is performed to increment a sensor cell open-circuit counter that indicates the number of times query step 114 has been satisfied. Step 118 is then performed to check whether the sensor cell open-circuit counter has reached a predefined value. When the predefined value is reached by the sensor cell open-circuit counter, step 120 is performed to turn ON a sensor cell open-circuit flag. It is then judged that there is an open circuit in the sensor cell 34. This judgment result appears, for instance, on a display device that is disposed in a vehicle interior. However, if it is found in step 114 that the amount of a sensor cell current change is equal to or greater than the predefined value, or if it is found in step 118 that the sensor cell open-circuit counter has not reached the predefined value, it is concluded that the sensor cell 34 is functioning normally. In this instance, step 122 is performed to turn OFF the sensor cell open-circuit flag.

When the ECU 50 activates the open-circuit detection mode described above, an open-circuit-induced fault in the pump cell 28 or sensor cell 34 is accurately detected. After the open-circuit detection mode is activated for fault detection, the apparatus reverts to the normal gas concentration measurement mode. In such an instance, it is conceivable that the oxygen concentration in the measurement target gas chamber 18 is varied from the oxygen concentration prevailing before open-circuit detection mode activation because the pump cell current changes when the applied voltage is swept. However, such an oxygen concentration change is extremely small when compared to a situation where atmospheric air is supplied from the outside as in the use of a conventional technology disclosed by Patent Document 3. Therefore, the NOx concentration measurement process can be resumed within a very short period of time after open-circuit detection mode termination. The oxygen concentration in the measurement target gas chamber 18 can be promptly restored to the previous level particularly when the applied voltage is vertically swept as indicated in FIG. 3A.

In the embodiments described above, the present invention is applied to a two-cell limiting current sensor, which comprises the pump cell and sensor cell. Alternatively, however, the present invention can also be applied to a multi-cell limiting current sensor. For example, the present invention is applicable to a limiting current sensor in which a sensor cell and a monitor cell are both positioned downstream of a pump cell. The monitor cell is a sensor for measuring the oxygen concentration in the measurement target gas chamber. Therefore, the monitor cell can achieve open-circuit detection in the same manner as the sensor cell described above.

The present invention can also be applied to an electromotive (mixed potential) sensor, which is disclosed, for instance, by Japanese Patent Laid-open No. 2000-180411. In the electromotive sensor, its first stage is provided with an oxygen concentration adjustment function (pump cell) and a detection section (sensor cell) for generating an electromotive force in accordance with the NOx concentration is positioned downstream of the pump cell. In this configuration, an open circuit in the sensor cell can be detected in accordance with a change in the output of the sensor cell, which occurs when the voltage applied to the pump cell is varied. Further, the present invention can be applied to an air-fuel ratio sensor, which is disclosed, for instance, by Patent Document 3, in addition to the foregoing embodiments of a NOx sensor.

As regards the foregoing embodiments of a sensor cell or other similar cell that permits the flow of a current to vary in accordance with the application voltage as is the case with the pump cell, open-circuit detection can be achieved in the same manner as for the pump cell. More specifically, an open circuit in the sensor cell can be detected in accordance with a change in the current that occurs when the voltage applied to the sensor cell reverts to a reference level after a temporary deviation from the reference level. In such a situation, the sensor cell needs to be provided with a variable power supply. However, an advantage is provided so that fault detection can be achieved by the sensor cell alone without regard to the pump cell status.

In the foregoing embodiments, the voltage variation means for the first and second aspects of the present invention is implemented by the variable power supply 54 and the ECU 50, which performs processing step 102. Further, the fault detection means for the first aspect of the present invention is implemented when the ECU 50 performs processing steps 104, 106, 108, and 110. Furthermore, the second cell fault detection means for the second aspect of the present invention is implemented when the ECU 50 performs processing steps 114, 116, 118, and 120.

The major benefits of the present invention described above are summarized follows:

In the first aspect of the present invention, the current flow caused by the cell follows the normal voltage-current characteristic and does not significantly vary from the limiting current when the applied voltage merely increases or decreases. However, when the applied voltage varies in an undulating manner, that is, when the applied voltage reverts to a reference level after a temporary deviation from the reference level, the current flow caused by the cell does not follow the normal voltage-current characteristic but varies in an undulating manner in response to the changes in the applied voltage. Therefore, the present invention makes it possible to vary the current flow caused by the cell without raising the voltage beyond the limiting current region, and detect a fault in the cell in accordance with a change in the current. As a fault in the cell is detected in accordance with a change in the current, which is caused by a change in the applied voltage, accurate fault detection can be achieved without being affected by the air-fuel ratio.

Although the oxygen concentration in the measurement target gas chamber varies with changes in the current flow caused by the cell, the degree of such variation is considerably smaller than in a case where atmospheric air is supplied from the outside. Therefore, the present invention ensures that the normal gas concentration measurement operation can be resumed within a short period of time after termination of fault detection.

In the second aspect of the present invention, the current flow caused by the first cell follows the normal voltage-current characteristic and does not significantly vary from the limiting current when the applied voltage merely increases or decreases. However, when the applied voltage varies in an undulating manner, that is, when the applied voltage reverts to a reference level after a temporary deviation from the reference level, the current flow caused by the first cell does not follow the normal voltage-current characteristic but varies in an undulating manner in response to the changes in the applied voltage. Therefore, the present invention makes it possible to vary the current flow caused by the first cell without raising the voltage beyond the limiting current region, vary the oxygen concentration in the measurement target gas chamber in accordance with the changes in the current, vary the output signal of the second cell in accordance with the changes in the oxygen concentration, and detect a fault in the second cell in accordance with a change in the output signal. As a fault in the second cell is detected in accordance with a change in the output signal of the second cell, which is caused by a change in the voltage applied to the first cell, accurate fault detection can be achieved without being affected by the air-fuel ratio.

Although the oxygen concentration in the measurement target gas chamber varies with changes in the current flow caused by the first cell, the degree of such variation is considerably smaller than in a case where atmospheric air is supplied from the outside. Therefore, the present invention ensures that the normal gas concentration measurement operation can be resumed within a short period of time after termination of fault detection.

The invention claimed is:

1. A gas concentration measurement apparatus comprising:
    a cell that comprises a solid electrolyte and a pair of electrodes on the surface of said solid electrolyte with one of the electrodes facing a measurement target gas chamber and causes, upon receipt of an applied voltage, a current to flow in accordance with the amount of oxygen discharge while discharging oxygen from said measurement target gas chamber;
    a power supply for applying a voltage to said cell;
    voltage variation means for varying the voltage by sweeping from a reference level to a predetermined level to be applied to said cell;
    current measurement means for measuring the current caused by said cell; and
    fault detection means for detecting an open-circuit in said cell in accordance with a change in the current caused by said cell during a sweep of the voltage, wherein
    the cell has a gas concentration measurement mode and an open-circuit detection mode, and the open-circuit detection mode is activated only periodically at appropriate time intervals,
    the sweep of the voltage is accomplished by superposing an AC voltage component over the applied voltage,
    only in the open-circuit detection mode is the sweep of the voltage applied, and
    an open-circuit is detected when a magnitude of a change in cell current is less than a predetermined amount when the sweep of the voltage is applied, and remains less than the predetermined amount for a predetermined number of applications of the sweep of the voltage.

2. The gas concentration measurement apparatus according to claim 1, wherein said voltage variation means varies the voltage applied to said cell periodically at a specified amplitude around the reference level.

3. The gas concentration measurement apparatus according to claim 1, wherein said fault detection means detects the fault in accordance with the magnitude of the change in the current caused by said cell.

4. The gas concentration measurement apparatus according to claim 1, wherein said gas concentration measurement apparatus is a NOx concentration sensor; and said cell is a pump cell of the NOx concentration sensor.

5. The gas concentration measurement apparatus according to claim 1, wherein said gas concentration measurement apparatus is an air-fuel ratio sensor; and said cell is a pump cell of the air-fuel ratio sensor.

6. A gas concentration measurement apparatus comprising:
a first cell that comprises a solid electrolyte and a pair of electrodes on the surface of said solid electrolyte with one of the electrodes facing a measurement target gas chamber and causes, upon receipt of an applied voltage, a current to flow in accordance with the amount of oxygen discharge while discharging oxygen from said measurement target gas chamber;
a second cell for generating a signal in accordance with the oxygen concentration in said measurement target gas chamber;
a power supply for applying a voltage to said first cell;
voltage variation means for varying the voltage by sweeping from a reference level to a predetermined level to be applied to said cell;
second cell output signal measurement means for measuring a signal that is generated from said second cell; and
second cell fault detection means for detecting a fault in said second cell in accordance with a change in the signal generated from said second cell during a sweep of the voltage, wherein
the first cell has a gas concentration measurement mode and an open-circuit detection mode, and the open-circuit detection mode is activated only periodically at appropriate time intervals,
the sweep of the voltage is accomplished by superposing an AC voltage component over the applied voltage,
only in the open-circuit detection mode is the sweep of the voltage applied,
an open-circuit is detected when a magnitude of a change in the first cell current is less than a predetermined amount when the sweep of the voltage is applied, and remains less than the predetermined amount for a predetermined number of applications of the sweep of the voltage, and
the second cell fault detection means does not operate to detect a fault in the second cell when an open-circuit is determined to occur in the first cell.

7. The gas concentration measurement apparatus according to claim 6, further comprising:
first cell current measurement means for measuring the current caused by said first cell;
first cell fault detection means for detecting a fault in said first cell in accordance with a change in the current caused by said first cell when the voltage applied to said first cell reverts to a reference level after a temporary deviation from the reference level.

8. The gas concentration measurement apparatus according to claim 6, wherein said voltage variation means varies the voltage applied to said first cell periodically at a specified amplitude around the reference level.

9. The gas concentration measurement apparatus according to claim 6, wherein said second cell fault detection means detect the fault in accordance with the magnitude of the change in the signal generated from said second cell.

10. The gas concentration measurement apparatus according to claim 6, wherein said gas concentration measurement apparatus is a NOx concentration sensor; said first cell is a pump cell of the NOx concentration sensor; and said second cell is a sensor cell of the NOx concentration sensor.

* * * * *